(12) United States Patent
Kawae

(10) Patent No.: US 8,257,261 B2
(45) Date of Patent: Sep. 4, 2012

(54) ULTRASONIC IMAGING APPARATUS AND IMAGE PROCESSING APPARATUS

(75) Inventor: Sotaro Kawae, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1077 days.

(21) Appl. No.: 12/177,840

(22) Filed: Jul. 22, 2008

(65) Prior Publication Data

US 2009/0030314 A1  Jan. 29, 2009

(30) Foreign Application Priority Data

Jul. 23, 2007   (JP) .................................. 2007-190483

(51) Int. Cl.
*A61B 8/00* (2006.01)
(52) U.S. Cl. ........................ 600/443; 600/407; 600/437
(58) Field of Classification Search .................. 600/437, 600/407, 444–445, 449, 453, 463; 382/128
See application file for complete search history.

(56) References Cited

U.S. PATENT DOCUMENTS

| | | | |
|---|---|---|---|
| 5,396,890 A | | 3/1995 | Weng |
| 5,454,371 A | | 10/1995 | Fenster et al. |
| 5,485,842 A | | 1/1996 | Quistgaard |
| 5,582,173 A | | 12/1996 | Li |
| 5,588,435 A | * | 12/1996 | Weng et al. .................. 600/443 |
| 5,787,889 A | | 8/1998 | Edwards et al. |
| 5,838,592 A | * | 11/1998 | Spratt ........................... 702/155 |
| 5,934,288 A | | 8/1999 | Avila et al. |
| 6,012,458 A | | 1/2000 | Mo et al. |
| 6,014,143 A | | 1/2000 | Naqvi et al. |
| 6,106,471 A | | 8/2000 | Wiesauer et al. |
| 6,171,244 B1 | | 1/2001 | Finger et al. |
| 6,263,093 B1 | | 7/2001 | Mochizuki |
| 6,338,716 B1 | | 1/2002 | Hossack et al. |
| 6,396,940 B1 | | 5/2002 | Carrott et al. |
| 6,416,476 B1 | * | 7/2002 | Ogasawara et al. ........... 600/443 |
| 6,417,857 B2 | | 7/2002 | Finger et al. |
| 6,450,962 B1 | | 9/2002 | Brandl et al. |
| 6,723,050 B2 | | 4/2004 | Dow et al. |
| 7,079,132 B2 | | 7/2006 | Sauer et al. |
| 7,126,599 B2 | | 10/2006 | Nishitani et al. |
| 7,251,352 B2 | | 7/2007 | Sauer et al. |
| 7,302,286 B2 | | 11/2007 | Camus et al. |

(Continued)

FOREIGN PATENT DOCUMENTS

JP   2005-051900   2/2005

*Primary Examiner* — Tse Chen
*Assistant Examiner* — Joel F Brutus
(74) *Attorney, Agent, or Firm* — Armstrong Teasdale LLP

(57) ABSTRACT

An ultrasonic imaging apparatus includes a 3D tomographic image data capturing device which captures 3D tomographic image data from a 3D region inside a subject, a region-of-interest setting device which sets a 3D region of interest corresponding to the 3D region in an image memory, a surface image extracting device which extracts data on a surface image, in the 3D region of interest, of a massive tissue included in the 3D region, a stereoscopic display generating device which generates stereoscopic display data, and a display device which displays the stereoscopic display data. The region-of-interest setting device displays a 2D tomographic image of a 2D region including the massive tissue on the display device, allows setting of a marker indicating a periphery of the massive tissue in the 2D tomographic image, and generates the 3D region of interest according to data on the marker's position.

20 Claims, 11 Drawing Sheets

U.S. PATENT DOCUMENTS

| | | |
|---|---|---|
| 7,343,195 B2 | 3/2008 | Strommer et al. |
| 2003/0055308 A1* | 3/2003 | Friemel et al. .................. 600/15 |
| 2003/0109779 A1* | 6/2003 | Ohishi et al. .................. 600/407 |
| 2003/0181813 A1* | 9/2003 | Ogawa .......................... 600/443 |
| 2005/0049503 A1* | 3/2005 | Schoisswohl et al. ........ 600/453 |
| 2005/0240104 A1* | 10/2005 | Shim et al. .................... 600/437 |

* cited by examiner

- 61 2D REGION OF INTEREST
- 63 AMNIOTIC FLUID
- 62 FETUS

- 65 CONTOUR IMAGE
- 64 CONTOUR

- 65 CONTOUR IMAGE
- 67 3D REGION OF INTEREST
- SURFACE IMAGE 66

ULTRASONIC IMAGING APPARATUS AND IMAGE PROCESSING APPARATUS

CROSS REFERENCE TO RELATED APPLICATIONS

This application claims the benefit of Japanese Patent Application No. 2007-190483 filed Jul. 23, 2007, and incorporated by reference in its entirety.

BACKGROUND OF THE INVENTION

The subject matter disclosed herein relates to an ultrasonic imaging apparatus and an image processing apparatus which extract a surface image of a massive tissue in a subject from 3D tomographic image data on the subject and display it stereoscopically.

Recently, in the field of diagnostic imaging using an ultrasonic imaging apparatus, volume rendering in which a surface image of a massive tissue such as a fetus is extracted according to 3D tomographic image data and displayed stereoscopically has been performed. This stereoscopic display makes it easy for an operator to get an overall picture of the massive tissue (for example, see Japanese Patent Application No. 2003-204963).

In this surface image extraction, positional information on a massive tissue region to be extracted is specified using a 2D region of interest as set in a corresponding 2D tomographic image. As for the 2D region of interest including the massive tissue region, the operator forms a borderline constituting the boundary of the 2D region of interest, using a cursor on the 2D tomographic image. A 3D region of interest is formed by automatically expanding the borderline in a direction orthogonal to the 2D tomographic image.

However, according to the above background art, the position of the stereoscopically displayed surface image of the massive tissue is not well balanced in the 3D region of interest. In other words, the boundary constituting the surface of the massive tissue falls within the 2D region of interest but may not fall within the automatically expanded 3D region of interest. If that is the case, a stereoscopic display of the surface image is not a stereoscopic display spreading all over the 3D region of interest but a stereoscopic display only in a limited part of the region.

Since the purpose of a stereoscopic display of a surface image is to enable one to grasp an overall picture of a massive tissue easily, a stereoscopic display only in a limited region is not desirable. Therefore, the operator has to set a 2D region of interest repeatedly so that the boundary constituting the surface of the massive tissue spreads all over the 3D region of interest, which means that it takes much time and labor to obtain a final stereoscopic display.

On the other hand, in a clinical scene, a subject will feel much relieved if an image of her fetus is stereoscopically shown to her. In this case, if it should take time and labor to make a stereoscopic display of the fetus after capturing 3D tomographic image data, it would be frustrating and undesirable for both the operator and the subject.

For the above reasons, it is imperative to realize an ultrasonic imaging apparatus and an image processing apparatus that easily and quickly set a 2D region of interest to maximize the spread of a boundary constituting the surface of a massive tissue over a 3D region of interest.

BRIEF DESCRIPTION OF THE INVENTION

It is desirable that the problems described previously are solved.

An ultrasonic imaging apparatus according to a first aspect of the invention is characterized by including a 3D tomographic image data capturing device which captures 3D tomographic image data from a 3D region inside a subject, a region-of-interest setting device which sets a 3D region of interest corresponding to the 3D region in an image memory that stores the 3D tomographic image data, a surface image extracting device which extracts data on a surface image, in the 3D region of interest, of a massive tissue included in the 3D region using the 3D tomographic image data, a stereoscopic display generating device which generates stereoscopic display data to display the surface image data stereoscopically, and a display device which displays the stereoscopic display data, wherein the region-of-interest setting device displays a 2D tomographic image of a 2D region including the massive tissue on the display device, allows manual setting of a marker indicating a periphery of the massive tissue in the 2D tomographic image, and generates the 3D region of interest with the marker in the vicinity of the center according to data on the marker's position in the 2D tomographic image.

According to the first aspect of the invention, the region-of-interest setting device generates a 3D region of interest in which a periphery of the massive tissue is almost centrally positioned.

An ultrasonic imaging apparatus according to a second aspect of the invention is characterized by including a 3D tomographic image data capturing device which captures 3D tomographic image data from a 3D region inside a subject, a region-of-interest setting device which sets a 3D region of interest corresponding to the 3D region in an image memory that stores the 3D tomographic image data, a surface image extracting device which extracts data on a surface image, in the 3D region of interest, of a massive tissue included in the 3D region using the 3D tomographic image data, a stereoscopic display generating device which generates stereoscopic display data to display the surface image data stereoscopically, and a display device which displays the stereoscopic display data, wherein the region-of-interest setting device includes a massive tissue cross section display device which displays a 2D tomographic image of a 2D region including the massive tissue, a massive tissue boundary setting device which allows a linear massive tissue boundary to be set manually on a periphery of the massive tissue appearing in the 2D tomographic image, a 2D region-of-interest generating device which generates a 2D region of interest including the massive tissue boundary in the vicinity of the center, and a 3D region-of-interest generating device which generates a 3D region of interest by expanding a region of interest of the same shape as the 2D region of interest, in a direction orthogonal to the 2D region.

According to the second aspect of the invention, in the region-of-interest setting device, the massive tissue cross section display device displays a 2D tomographic image of a 2D region including the massive tissue, the massive tissue boundary setting device allows a linear massive tissue boundary to be set manually on a periphery of the massive tissue appearing in the 2D tomographic image, the 2D region-of-interest generating device generates a 2D region of interest including the massive tissue boundary in the vicinity of the center, and the 3D region-of-interest generating device generates a 3D region of interest by expanding a region of interest of the same shape as the 2D region of interest, in a direction orthogonal to the 2D region.

The ultrasonic imaging apparatus according to a third aspect of the invention, in the ultrasonic imaging apparatus of the second aspect, further includes an orthogonal 3-sectional plane formation device to form tomographic image data on three orthogonal sectional planes which are orthogonal to each other in the 3D region.

According to the third aspect of the invention, a main tomographic image data portion of 3D tomographic image data is extracted from tomographic image data on three orthogonal sectional planes.

The ultrasonic imaging apparatus according to a fourth aspect of the invention is characterized in that, in the ultrasonic imaging apparatus of the third aspect, the display device displays tomographic image data on the three orthogonal sectional planes.

According to the fourth aspect of the invention, an operator easily grasps the main content of the 3D tomographic image data from the displayed tomographic image data on the three orthogonal sectional planes.

The ultrasonic imaging apparatus according to a fifth aspect of the invention is characterized in that, in the ultrasonic imaging apparatus according to any of the second to fourth aspects, the 3D tomographic image data capturing device includes a probe array in which piezoelectric elements are one-dimensionally arranged in an arc or linear pattern, and an ultrasonic probe which mechanically scans the probe array repeatedly in a mechanical scan direction orthogonal to the direction of the one-dimensional arrangement.

According to the fifth aspect of the invention, 3D tomographic image data is captured in real time by mechanically scanning the one-dimensionally arranged probe array.

The ultrasonic imaging apparatus according to a sixth aspect of the invention is characterized in that, in the ultrasonic imaging apparatus according to the fifth aspect, the orthogonal 3-sectional plane formation device forms, as one of the three orthogonal sectional planes, a sectional plane including an electronic scan direction as the direction of the one-dimensional arrangement and, as another of the three orthogonal sectional planes, a plane including the mechanical scan direction.

According to the sixth aspect of the invention, the sectional planes among the three orthogonal sectional planes are made to coincide with the electronic scan direction and mechanical scan direction.

The ultrasonic imaging apparatus according to a seventh aspect of the invention is characterized in that, in the ultrasonic imaging apparatus according to the sixth aspect, the massive tissue cross section display device makes the 2D region coincide with the sectional plane including the electronic scan direction, among the three orthogonal sectional planes.

According to the seventh aspect of the invention, the 2D region of interest is set in a sectional plane oriented in the electronic scan direction.

The ultrasonic imaging apparatus according to an eighth aspect of the invention is characterized in that, in the ultrasonic imaging apparatus according to any of the second to fourth aspects, the 3D tomographic image data capturing device includes an ultrasonic probe having a 2D probe array in which piezoelectric elements are two-dimensionally arranged in a planar pattern.

According to the eighth aspect of the invention, 3D tomographic image data is captured more quickly by the 2D probe array.

The ultrasonic imaging apparatus according to a ninth aspect of the invention is characterized in that, in the ultrasonic imaging apparatus according to any of the second to eighth aspects, the massive tissue boundary setting device includes a marker setting device which sets two markers on the 2D tomographic image and takes a line connecting the two markers as the massive tissue boundary.

According to the ninth aspect of the invention, a massive tissue boundary included in the 2D tomographic image is easily specified.

The ultrasonic imaging apparatus according to a tenth aspect of the invention is characterized in that, in the ultrasonic imaging apparatus according to any of the second to ninth aspects, the 2D region-of-interest generating device generates a 2D region of interest which is comprised of two regions of equal areas with the massive tissue boundary between them.

According to the tenth aspect of the invention, the massive tissue boundary is positioned in the vicinity of the center of the 2D region of interest.

The ultrasonic imaging apparatus according to an eleventh aspect of the invention is characterized in that, in the ultrasonic imaging apparatus according to any of the second to ninth aspects, the 2D region-of-interest generating device generates a 2D region of interest which is comprised of two regions of almost equal lengths in a direction orthogonal to the massive tissue boundary in the 2D tomographic image with the massive tissue boundary between them.

According to the eleventh aspect of the invention, the massive tissue boundary is positioned in the vicinity of the center of the 2D region of interest.

The ultrasonic imaging apparatus according to a twelfth aspect of the invention is characterized in that, in the ultrasonic imaging apparatus according to any of the second to eleventh aspects, the 3D region-of-interest generating device positions the 2D region of interest centrally in a direction orthogonal to the 2D region of interest in the 3D region of interest.

According to the twelfth aspect of the invention, the massive tissue boundary is positioned in the vicinity of the center of the 2D region of interest and spreads all over the 3D region of interest more surely.

The ultrasonic imaging apparatus according to a thirteenth aspect of the invention is characterized in that, in the ultrasonic imaging apparatus according to any of the second to twelfth aspects, the 3D region-of-interest generating device includes an input device to enter a size to which the 2D region of interest is expanded in a direction orthogonal to the 2D region of interest.

According to the thirteenth aspect of the invention, the size of the 3D region of interest in the direction orthogonal to the 2D region is adjusted.

The ultrasonic imaging apparatus according to a fourteenth aspect of the invention is characterized in that, in the ultrasonic imaging apparatus according to any of the second to thirteenth aspects, the surface image extracting device includes an input device to enter a threshold used in extracting surface image data from the 3D tomographic image data in the 3D region of interest, using pixel values.

According to the fourteenth aspect of the invention, a surface image and a stereoscopic display of the surface image are clear with less noise.

The ultrasonic imaging apparatus according to a fifteenth aspect of the invention is characterized in that, in the ultrasonic imaging apparatus according to any of the second to fourteenth aspects, the stereoscopic display generating device displays the surface image data in shaded form.

According to the fifteenth aspect of the invention, due to shading, the stereoscopic display is easy to understand.

An image processing apparatus according to a sixteenth aspect of the invention is characterized by including an image memory which stores 3D tomographic image data in a subject, a region-of-interest setting device which sets a 3D region of interest in a 3D region in which the 3D tomographic image data is captured, a surface image extracting device which extracts data on a surface image of a massive tissue included in the 3D region of interest using the 3D tomographic image data, a stereoscopic display generating device which generates stereoscopic display data to display the surface image data stereoscopically, and a display device which displays the stereoscopic display data, wherein the region-of-interest setting device includes a massive tissue cross section display device which displays a 2D tomographic image of a 2D region including the massive tissue, a massive tissue boundary setting device which allows a linear massive tissue boundary to be set manually on a periphery of the massive tissue appearing in the 2D tomographic image, a 2D region-of-interest generating device which generates a 2D region of interest including the massive tissue boundary in the vicinity of the center, and a 3D region-of-interest generating device which generates a 3D region of interest by expanding a region of interest of the same shape as the 2D region of interest, in a direction orthogonal to the 2D region.

In one embodiment, a 2D region of interest is set so that the massive tissue boundary is included in the 3D region of interest to the maximum extent, and therefore an optimum stereoscopic image is obtained from the beginning and the trouble of setting a 2D region of interest repeatedly is saved and an optimum surface image is easily and quickly displayed.

Further objects and advantages of the embodiments of the present invention described herein will be apparent from the following description as illustrated in the accompanying drawings.

DETAILED DESCRIPTION OF THE INVENTION

Next, embodiments of the invention as an ultrasonic imaging apparatus will be described referring to the accompanying drawings. It does not limit the invention.

Figure 1:
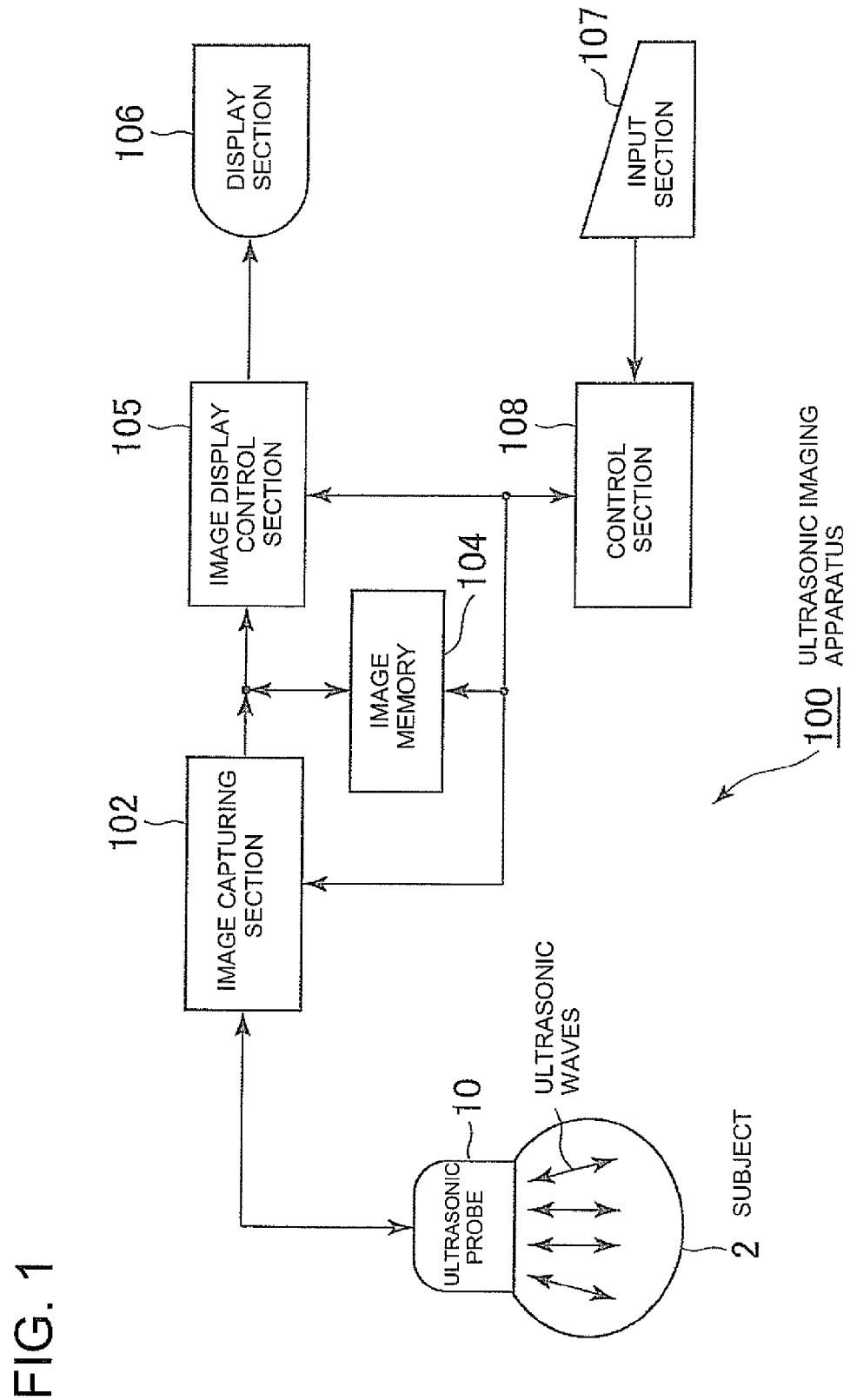
FIG. 1 is a block diagram showing the general structure of an ultrasonic imaging apparatus.

First, the general structure of an ultrasonic imaging apparatus 100 according to this embodiment will be described. FIG. 1 is a block diagram showing the general structure of the ultrasonic imaging apparatus 100 according to this embodiment. The ultrasonic imaging apparatus 100 includes an ultrasonic probe 10, an image capturing section 102, an image memory 104, an image display control section 105, a display section 106, an input section 107, and a control section 108. Here, the ultrasonic probe 10, the image capturing section 102, the image memory 104 and the control section 108's image capture controller (which will be described later) constitute a 3D tomographic image data capturing means.

The ultrasonic probe 10 is a part which transmits or receives ultrasonic waves, namely radiates ultrasonic waves in a specific direction of a sectional plane of a subject 2 and receives ultrasonic echoes reflected each time from the inside of the subject 2 as temporally successive sound rays. On the other hand, the ultrasonic probe 10 performs an electronic scan and a mechanical scan while changing the direction of ultrasonic radiation successively. As will be detailed later, the ultrasonic probe 10, which includes a probe array as piezoelectric elements arranged in an array pattern in the electronic scan direction, and a mechanical scanning means for mechanically scanning the probe array orthogonally to this arrangement, captures 3D tomographic image data from a 3D region inside the subject 2.

The image capturing section 102 includes a transceiver, a B-mode processor, and a Doppler processor. The transceiver, which is connected with the ultrasonic probe 10 by a coaxial cable, generates an electrical signal to activate the piezoelectric elements of the ultrasonic probe 10. The transceiver also carries out first-stage amplification of reflected ultrasonic echoes that it has received.

The B-mode processor performs processing to generate, in real time, a B-mode image from a reflected ultrasonic echo signal amplified by the transceiver and the Doppler processor extracts phase change information from the reflected ultrasonic echo signal amplified by the transceiver and calculates, in real time, blood flow data such as average velocity as average frequency in frequency shift, power and variance.

The image memory 104 is a large capacity memory which stores the B-mode image data captured by the image capturing section 102, Doppler image data including blood flow data and similar data. The image memory 104 is, for example, a hard disk or the like.

The image display control section 105 performs display frame rate conversion for the B-mode image data generated by the B-mode processor and the blood flow data generated by the Doppler processor and controls the image display form or position.

The display section 106 includes a CRT (Cathode Ray Tube) or LCD (Liquid Crystal Display) and displays a B-mode image or Doppler image or the like.

The input section 107 includes a keyboard and a mouse or the like and an operator enters an operation input signal through it. At the input section 107, an entry operation is made to select a B-mode display or Doppler processing display, an entry operation with a cursor or the like is made to perform image processing of the displayed image data or an entry operation is made to specify the Doppler imaging area for Doppler processing. Furthermore, information for mechanically scanning the probe array of the ultrasonic probe 10, such as scan mode, mechanical scan speed, maximum oscillation angle and scan start, is sent from the input section 107 to the control section 108.

The control section 108 includes an image capture controller which controls operation of components of the ultrasonic imaging apparatus including the ultrasonic probe according to the operation input signal entered through the input section 107 and the stored program or data, and an image processor which performs image processing using 3D tomographic image data stored in the image memory 104. The image capture controller controls the position of the probe array inside the ultrasonic probe 10 according to information on the ultrasonic probe 10 sent from the input section 107 such as scan mode, mechanical scan speed, maximum oscillation angle and scan start. The image processor of the control section 108 will be described in detail later.

Figure 2:
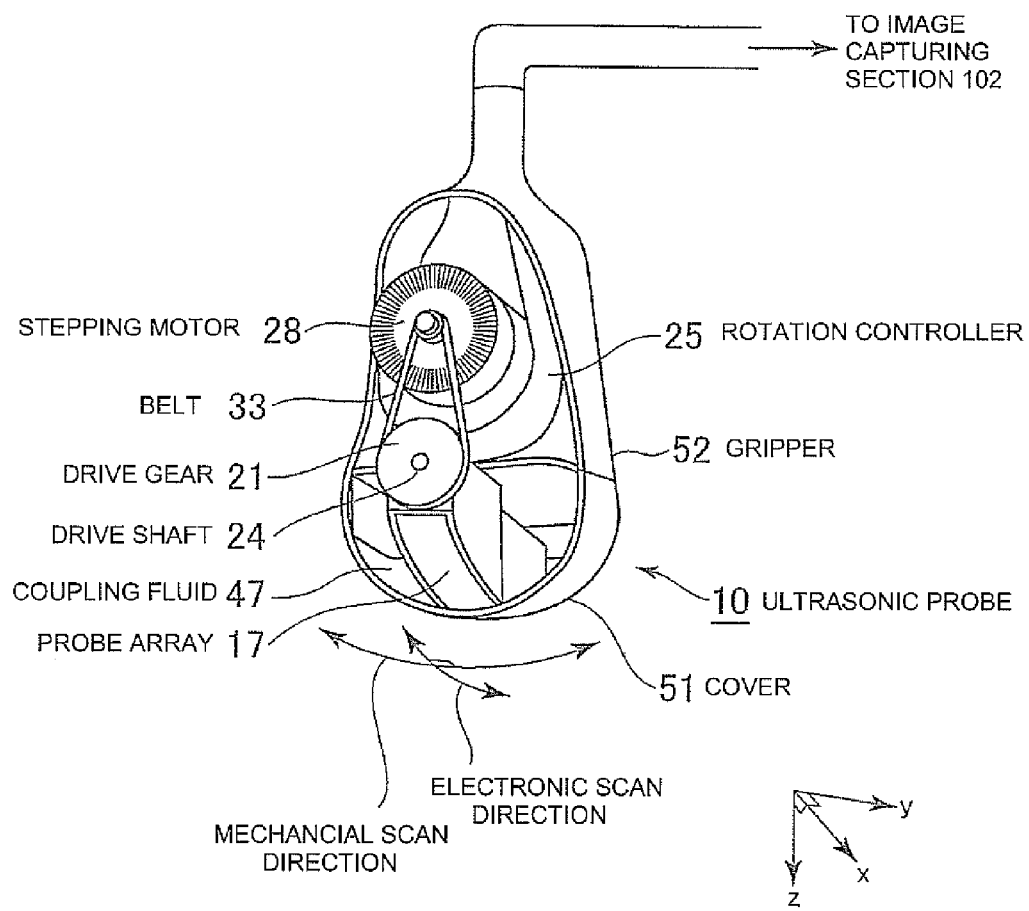
FIG. 2 is a sectional view showing the structure of an ultrasonic probe according to an embodiment.

FIG. 2 is a probe sectional view showing the internal structure of the ultrasonic probe 10. The ultrasonic probe 10 includes a cover 51, a gripper 52, a probe array 17, a coupling fluid 47, and a drive gear 21, a drive shaft 24, a stepping motor 28, a belt 33 and a rotation controller 25 which constitute a mechanical scanning means. Here the cover 51 and gripper 52 constitute a case which houses the probe array 17, coupling fluid 47, and the drive gear 21, stepping motor 28, belt 33 and rotation controller 25 which constitute the mechanical scanning means. The x, y and z coordinate axes shown in the figure are common to all the drawings with such coordinate axes and suggest positional relations among the drawings. Here, the x axis is oriented in the electronic scan direction, the y axis in the mechanical scan direction, and the z axis in the longitudinal direction of the gripper 52.

The cover 51, made of translucent film, has the shape of an arc along the trajectory of the probe array 17 to be mechanically scanned in an arc pattern. The material of the cover 51 is an acoustic impedance material that transmits ultrasonic waves generated by the probe array 17 and reflected ultrasonic echoes from the subject 2 with low loss.

The gripper 52 is made of moldable plastic or similar material and has a shape that allows the operator to hold the ultrasonic probe 10 easily and firmly.

The probe array 17 has a convex linear scan type probe. This linear scan type probe has a plurality of piezoelectric elements arranged in an array pattern in the electronic scan direction orthogonal to the mechanical scan direction and performs an electronic scan along this arrangement.

The probe array 17 performs a mechanical scan in the mechanical scan direction by the mechanical scanning means. The mechanical scanning means has the drive shaft 24, an oscillating means which lies along the electronic scan direction. As the drive shaft 24 rotates, the probe array 17's probe surface in contact with the cover 51 oscillates along an arc trajectory in the mechanical scan direction. The inside of the cover 51 in which the probe array 17 lies is filled with coupling fluid 47 where there is least loss in acoustic coupling between the probe array 17 and the cover 51.

The drive shaft 24 is mechanically connected with the stepping motor 28 through the drive gear 21 and belt 33. The stepping motor 28 rotates a given angle with high accuracy as intended upon input of control pulses from the rotation controller 25. With this rotation, the mechanically connected drive shaft 24 and probe array 17 rotate in the mechanical scan direction as well.

The rotation controller 25 has a pulse generator that generates pulses to drive the stepping motor 28 and a pulse controller that controls the pulses. The rotation controller 25 controls the stepping motor 28 and the rotation angle of the probe array 17 according to control information from the image capturing section 10 to oscillate the probe array 17 with the drive shaft 24 as the center of rotation.

For example, when no scan is made, the rotation controller 25 lets the probe array 17 stay at the home position where it is oriented in the z-axis direction fully facing the subject. The rotation controller 25 starts scanning from the home position in a given mechanical scan direction according to the probe array 17's maximum oscillation angle measured from its frontal position opposite to the subject and the probe array 17's scan speed in the mechanical scan direction which have been entered through the input section 107 by the operator. After that, upon receipt of an instruction to stop scanning from the input section 107 as given by the operator, the rotation controller 25 returns the probe array 17 to the home position and stops scanning.

Figure 3:
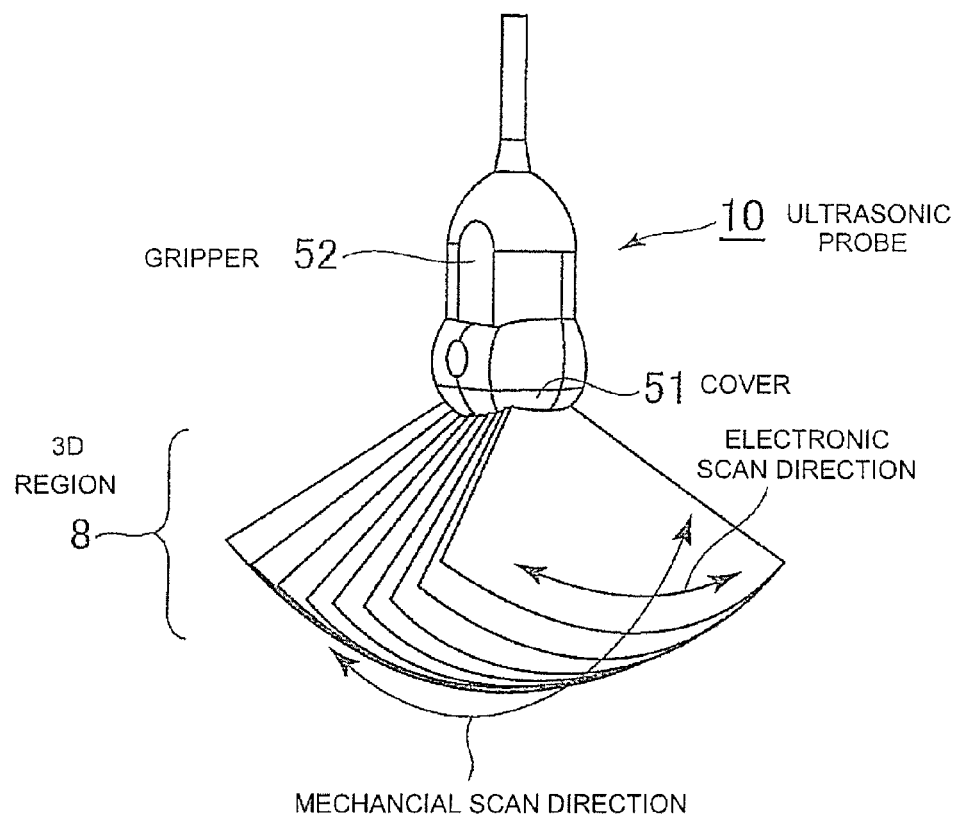
FIG. 3 is an explanatory view showing 3D operation of the ultrasonic probe according to the embodiment.

FIG. 3 is an explanatory view which schematically shows scans in the electronic scan direction and the mechanical scan direction orthogonal to the electronic scan direction which are performed using the ultrasonic probe 10, and a 3D region 8 inside the subject 2 which is captured during scanning. The ultrasonic probe 10 performs an electronic scan in the electronic scan direction in which the piezoelectric elements of the probe array 17 are arrayed, and captures tomographic image data. Then, the ultrasonic probe 10 moves the probe array 17 in the mechanical scan direction orthogonal to the electronic scan direction and again performs an electronic scan there to capture tomographic image data and repeats this sequence. 3D tomographic image data in the 3D region 8 inside the subject 2 is thus captured.

Figure 4:
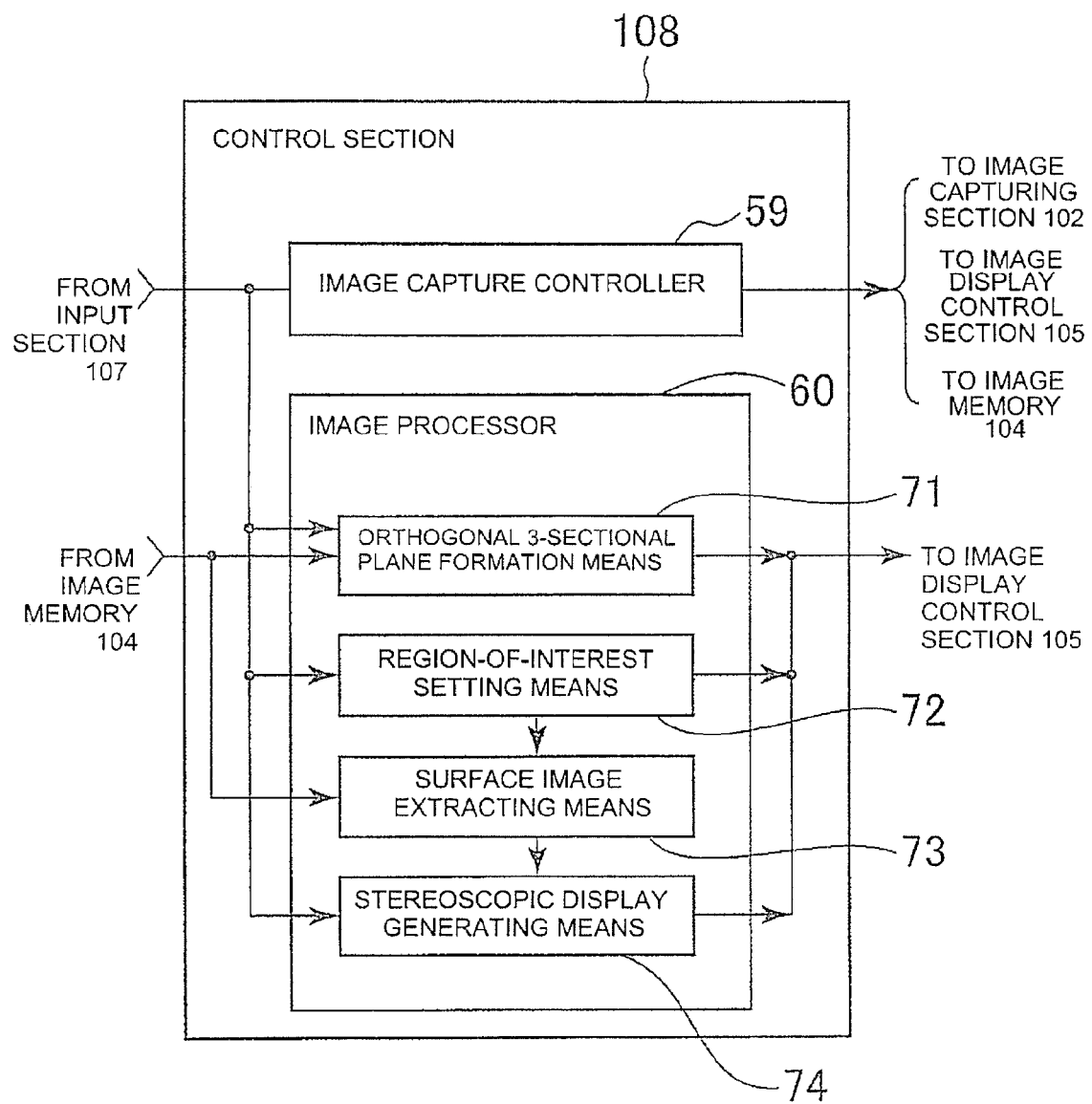
FIG. 4 is a functional block diagram showing the functional structure of the control section according to the embodiment.

FIG. 4 is a functional block diagram showing the functional structure of the control section 108. The control section 108 includes an image capture controller 59 and an image processor 60 and further the image processor 60 includes an orthogonal 3-sectional plane formation means 71, a region-of-interest setting means 72, a surface image extracting means 73 and a stereoscopic display generating means 74.

The image capture controller 59 captures 3D tomographic image data in the 3D region 8 as shown in FIG. 3 and stores it in a 3D memory area of the image memory 104. The 3D memory area is an address space that corresponds to the 3D region 8 where the captured tomographic image data in different spots of the 3D region 8 are stored at corresponding addresses.

The orthogonal 3-sectional plane formation means 71 forms 2D tomographic image data on three orthogonal sectional planes which are orthogonal to each other in the 3D region 8, according to the 3D tomographic image data stored in the 3D memory area of the image memory 104.

Figure 5:
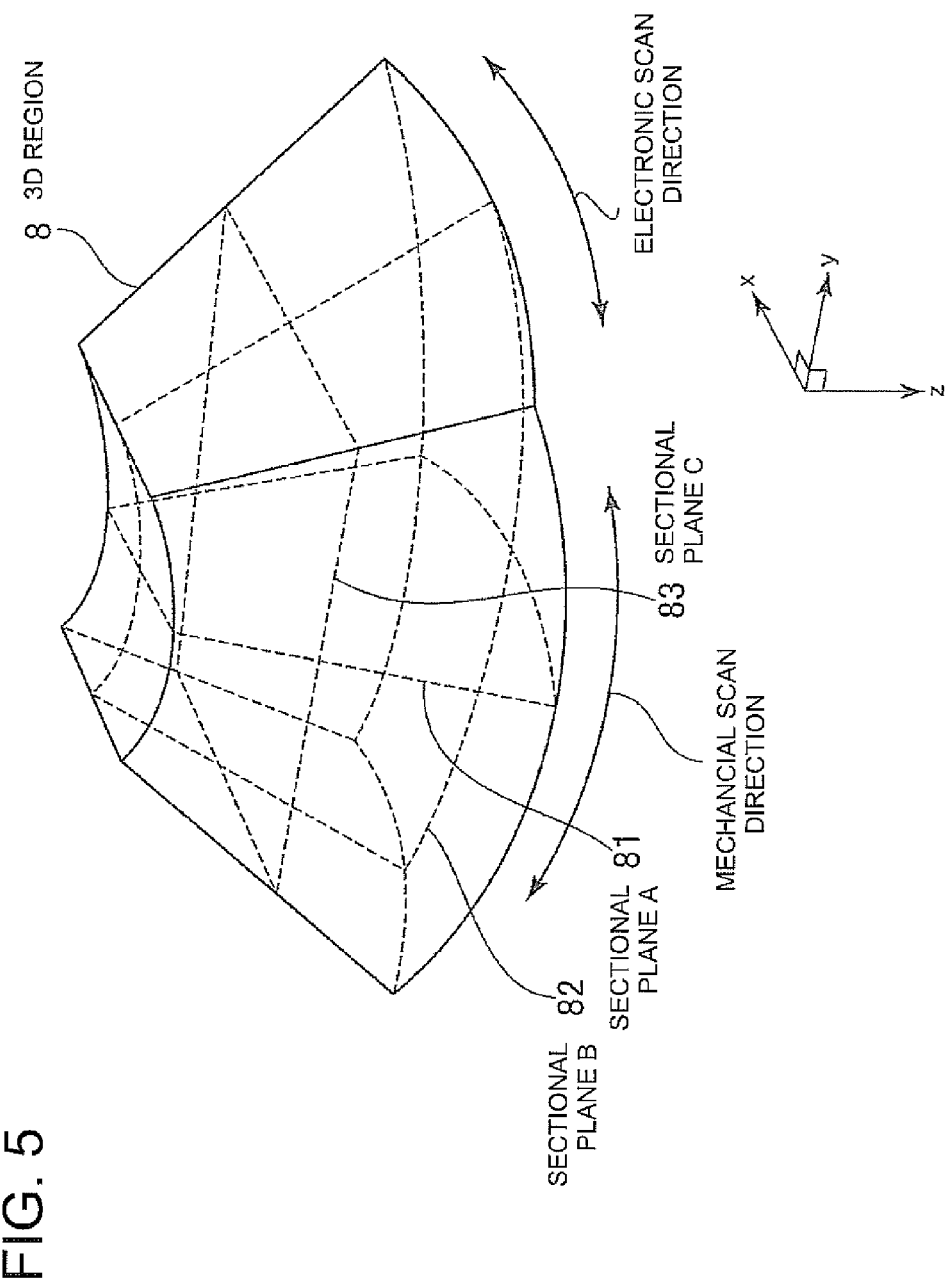
FIG. 5 is an explanatory view showing a 3D region captured by the ultrasonic probe and three orthogonal sectional planes in the 3D region.

FIG. 5 is an explanatory view schematically showing three orthogonal sectional planes set in the 3D region 8. The three orthogonal sectional planes are sectional plane A 81, sectional plane B 82, and sectional plane C 83. The sectional plane A 81 is parallel to the x-z axis plane and represents a sectional plane in the electronic scan direction at the home position. The sectional plane B 82 is parallel to the y-z axis plane and represents a sectional plane in the mechanical scan direction. The sectional plane C 83 is parallel to the x-y axis plane and is an opposite sectional plane facing the plane of contact of the ultrasonic probe 10 with the subject 2. The position of the sectional plane A 81 in the mechanical scan direction, the position of the sectional plane B 82 in the electronic scan direction and the depth position of the sectional plane C 83 from the plane of contact of the ultrasonic probe 10 with the subject 2 can be changed by an instruction from the input section 107.

The orthogonal 3-sectional plane formation means 71 extracts tomographic image data from 3D memory areas of the image memory 104 which correspond to the sectional plane A 81, sectional plane B 82 and sectional plane C 83 of the 3D region 8 and displays it on the display section 106. For these tomographic images, the frame rate at which the images are rewritten is lower than that for a single 2D B-mode image but the image data is updated almost in real time.

The region-of-interest setting means 72 sets a 3D region of interest in the 3D memory area of the image memory 104 corresponding to the 3D region. The 3D region of interest is set so as to include a massive tissue such as a fetus in the womb. How to set a 3D region of interest will be detailed later.

The surface image extracting means 73 extracts surface image data on a massive tissue from the 3D tomographic image data in the set 3D region of interest. This extraction process extracts, for example, 3D tomographic image data in a 3D region of interest obtained by expanding a 2D region of interest in a sectional plane parallel to the sectional plane A 81 in the y-axis direction as shown in FIG. 5. Then, using the 3D tomographic image data, a surface image contour is extracted in each 2D tomographic image of each 2D region of interest and a single surface image is formed by arranging these contours in the y-axis direction. For example, if the subject 2 is a pregnant woman, the ultrasonic probe 10 is placed on her abdominal area so that a surface image of the fetus in the womb is formed using 3D tomographic image data on the whole womb.

Figure 6A:
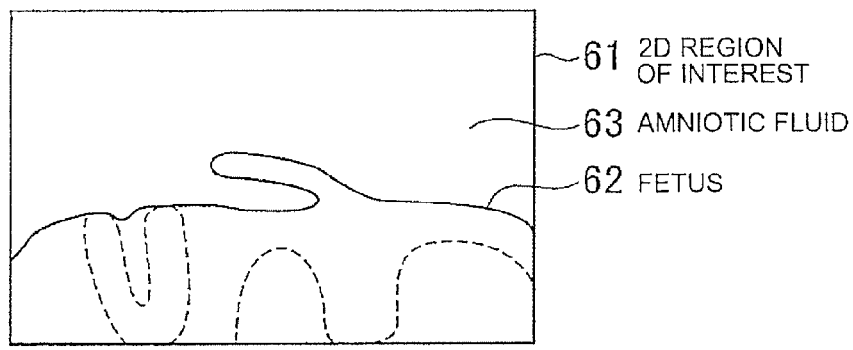
FIGS. 6A, 6B, and 6C are explanatory views showing the process of generating a surface image from a 2D region of interest set in a sectional plane A.
Figure 6B:
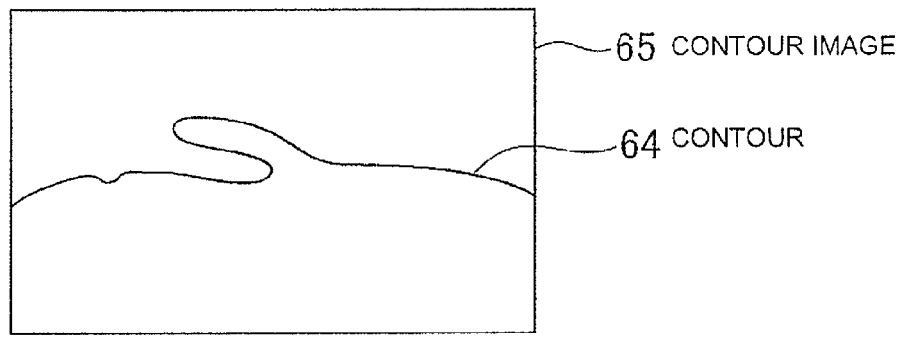
Figure 6C:
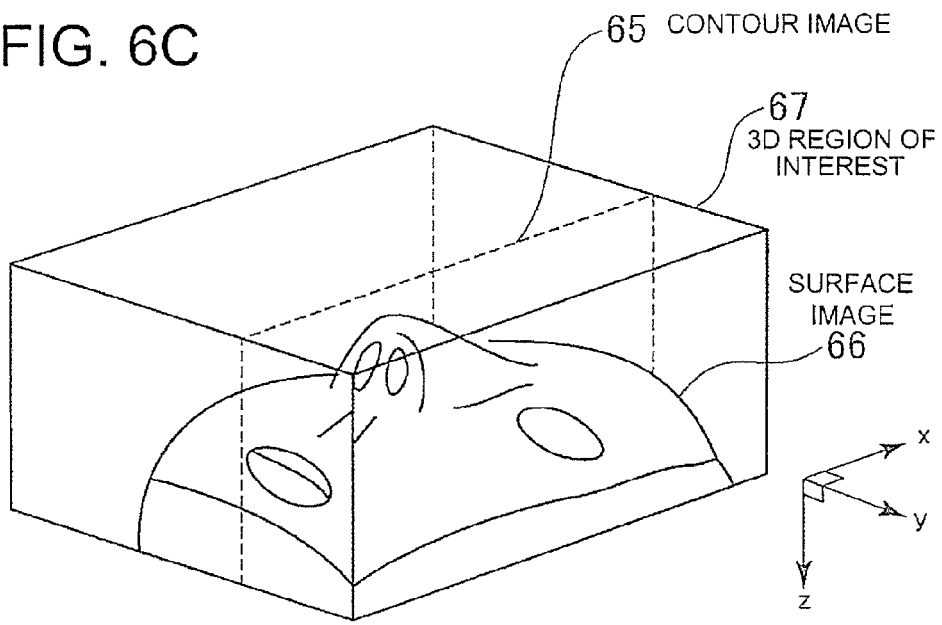

FIGS. 6A, 6B, and 6C are explanatory views schematically showing a process in which a contour is obtained from data on each 2D tomographic image and such contours are combined to create a surface image. Although the 2D region of interest and 3D region of interest as shown in FIG. 6A and FIG. 6C have the shape of a rectangle and a rectangular parallelpiped respectively for easy understanding, actually a 2D region of interest set in a 2D tomographic image is fan-shaped and also the relevant 3D region of interest 67 has a shape similar to the 3D region shown in FIG. 5.

FIG. 6A is an example of a 2D region of interest 61 parallel to the sectional plane 81 in the 3D region of interest. A tomographic image of a fetus 62 as a massive tissue appears in the lower part of the 2D region of interest 61 and an amniotic fluid 63 is seen in the upper part thereof.

FIG. 6B is a contour image 65 obtained by extraction of a contour line 64 on the surface of the fetus 62 from the 2D region of interest 61 shown in FIG. 6A. Here, in contour extraction, assuming that the intensity of reflected ultrasonic echoes at contours should be higher than at surrounding tissues, using an experimentally determined initial threshold or a threshold specified through the input section 107, the contour 64 is obtained by selecting pixel points that exceed the threshold.

FIG. 6C is a surface image 66 created in a 3D region of interest 67 by arranging contour images similar to the contour image 65 in the sectional plane A 81 as obtained in FIG. 6B along the y-axis direction. The facial shape of the fetus 62 is roughly created by an array of contour images 65. The 3D region of interest 67 is a region set inside the 3D region 8 by the region-of-interest setting means 72 and will be described in detail later. The x, y and z coordinate axes shown in FIG. 6C represent the positional relation of FIG. 6C with other figures but do not represent any positional relations of FIGS. 6A and 6B.

The stereoscopic display generating means 74 generates stereoscopic display data obtained by doing rendering such as shading on the surface image 66 extracted by the surface image extracting means 73 and displays it on the screen of the display section 106. For stereoscopic display of the surface image 66, stereoscopic display data is created by specifying the direction of the operator's line of sight or the like through the input section 107 and doing shading using a diffused reflection surface model or the like.

Figure 7:
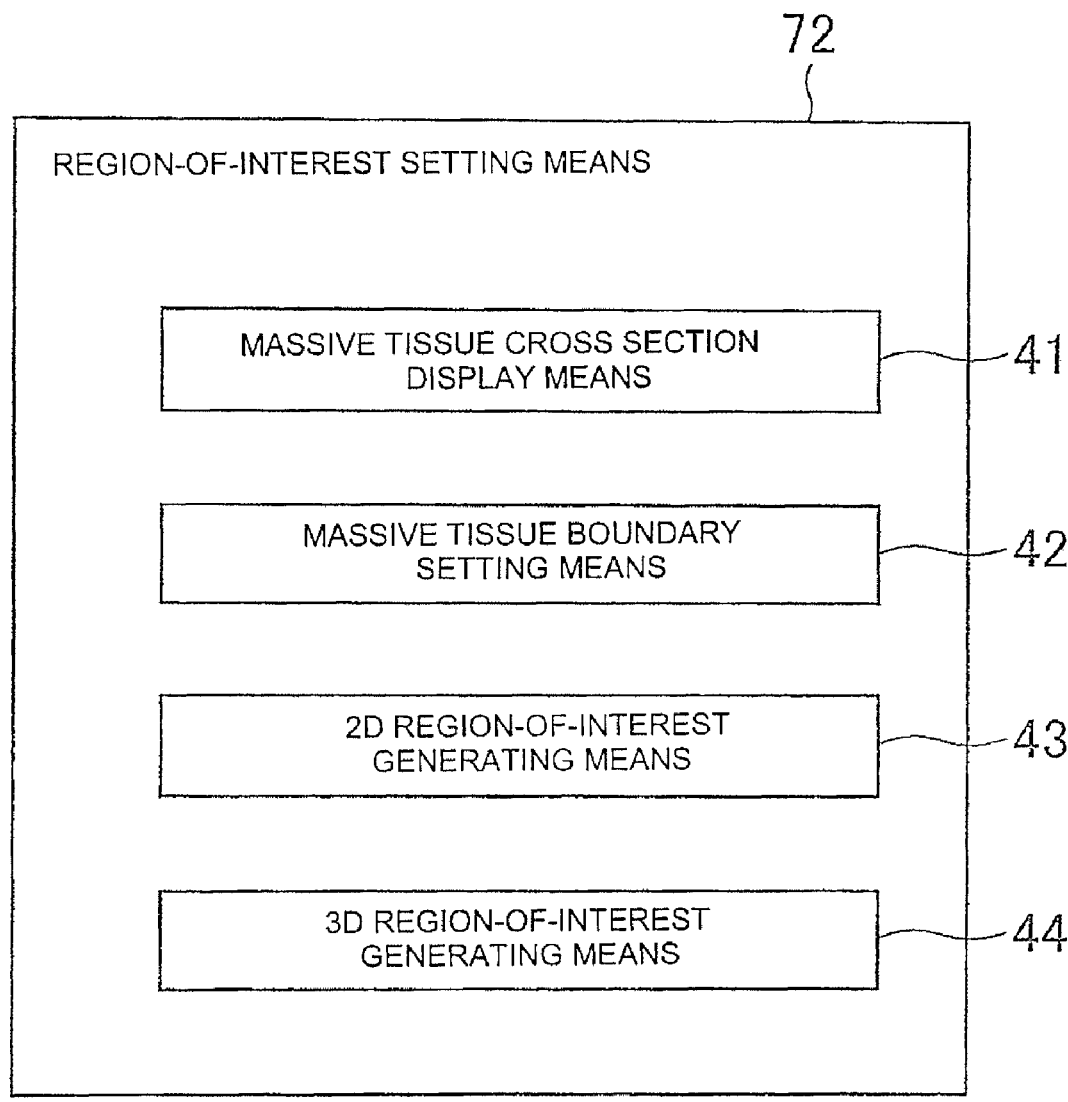
FIG. 7 is a block diagram showing the functional structure of a region-of-interest setting means according to the embodiment.

FIG. 7 is a block diagram showing the detailed functional structure of the region-of-interest setting means 72 for setting a 3D region of interest 67 as shown in FIG. 6. The region-of-interest setting means 72 includes a massive tissue cross section display means 41, a massive tissue boundary setting means 42, a 2D region-of-interest generating means 43, and a 3D region-of-interest generating means 44. The functions of the massive tissue cross section display means 41, massive tissue boundary setting means 42, 2D region-of-interest generating means 43 and 3D region-of-interest generating means 44 will be explained in detail below in connection with operation of the region-of-interest setting means 72.

Figure 8:
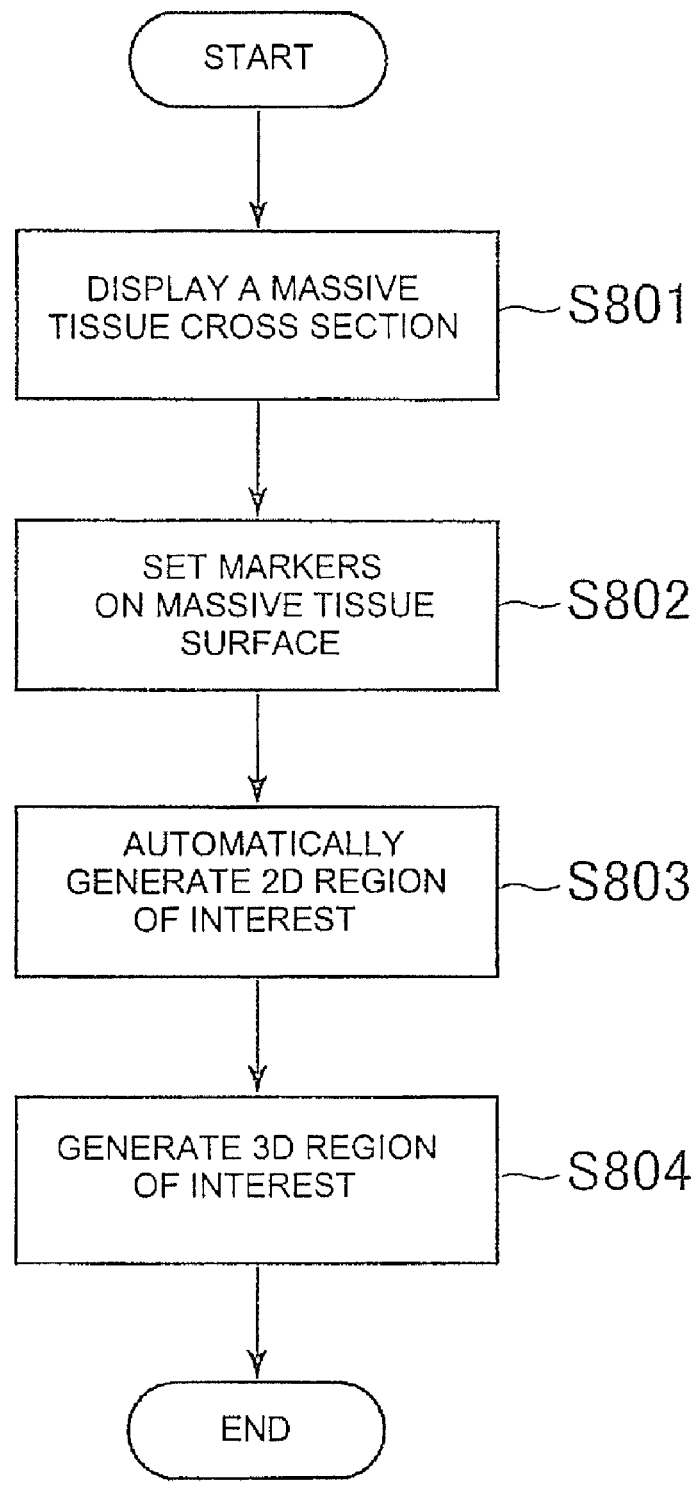
FIG. 8 is a flowchart showing operation of the region-of-interest setting means according to the embodiment.

Next, operation of the region-of-interest setting means 72 will be explained referring to FIG. 8. FIG. 8 is a flowchart showing operation of the region-of-interest setting means 72. First, the operator displays 2D tomographic image data on a massive tissue inside the subject 2, for example a fetus, on the display section 106 by the massive tissue cross section display means 41 (Step S801). The massive tissue cross section display means 41 displays 2D tomographic image data on the sectional plane A 81 as extracted from the 3D tomographic image data captured by the ultrasonic probe 10 by the orthogonal 3-sectional plane formation means 71. Here, the sectional plane A 81 is data on a tomographic image in the electronic scan direction at the home position that is central in the mechanical scan direction.

Figure 9A:
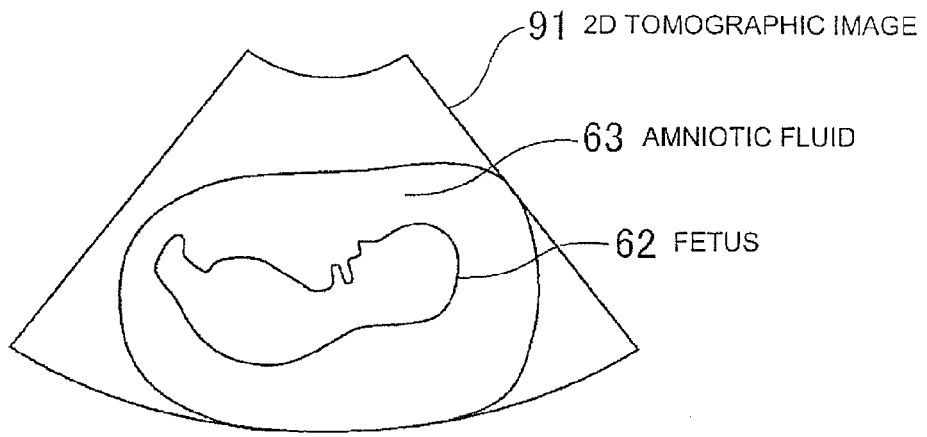
FIGS. 9A, 9B, and 9C are explanatory views showing markers set in 2D tomographic images in the sectional plane A.

FIG. 9A is an example of a 2D tomographic image 91 including a tomographic image of the fetus 62 in the sectional plane A 81 at the home position as shown in FIG. 5. The operator presses the ultrasonic probe 10 on the subject 2 in a way that a 2D tomographic image 91 containing the amniotic fluid 63 and fetus 62 comes in the sectional plane A 81 of the 3D region 8.

Figure 9B:
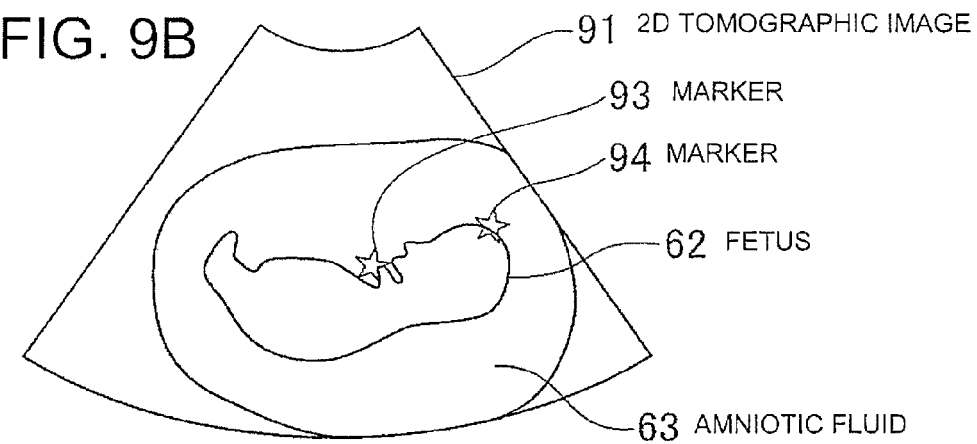

Then, the operator sets two markers 93 and 94 along the surface of the fetus 62 appearing as a massive tissue in the 2D tomographic image 91 by the massive tissue boundary setting means 42 (Step S802). The massive tissue boundary setting means 42 puts two markers 93 and 94 along an almost linear surface of the fetus 62 in the 2D tomographic image 91 by a marker setting means such as a cursor positioning mouse or trackball. FIG. 9B illustrates two markers 93 and 94 set on the image of the fetus 62. FIG. 9B shows that the two markers 93 and 94 have been set along the face of the fetus 62 which is almost linear, using a mouse or trackball.

Figure 9C:
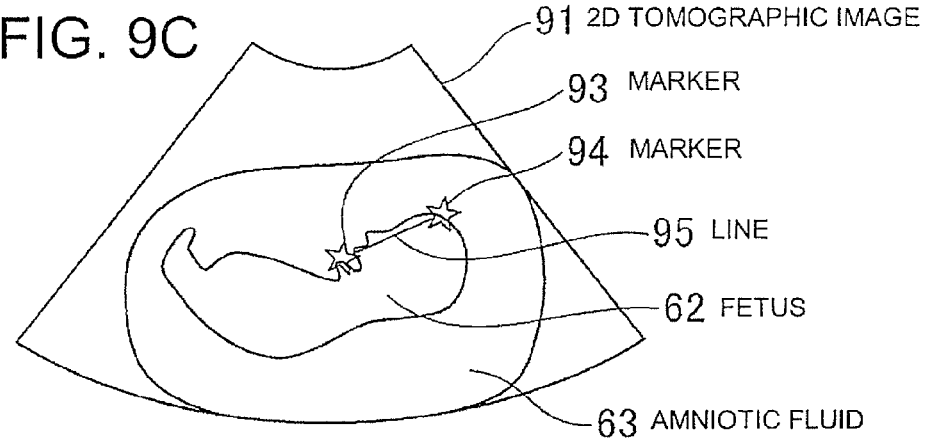

FIG. 9C is an explanatory view showing line 95 which connects the markers 93 and 94 set in the 2D tomographic image 91. Here, the line 95 connecting the markers 93 and 94 virtually traces the face of the fetus 62, indicating the massive tissue boundary.

Figure 10:
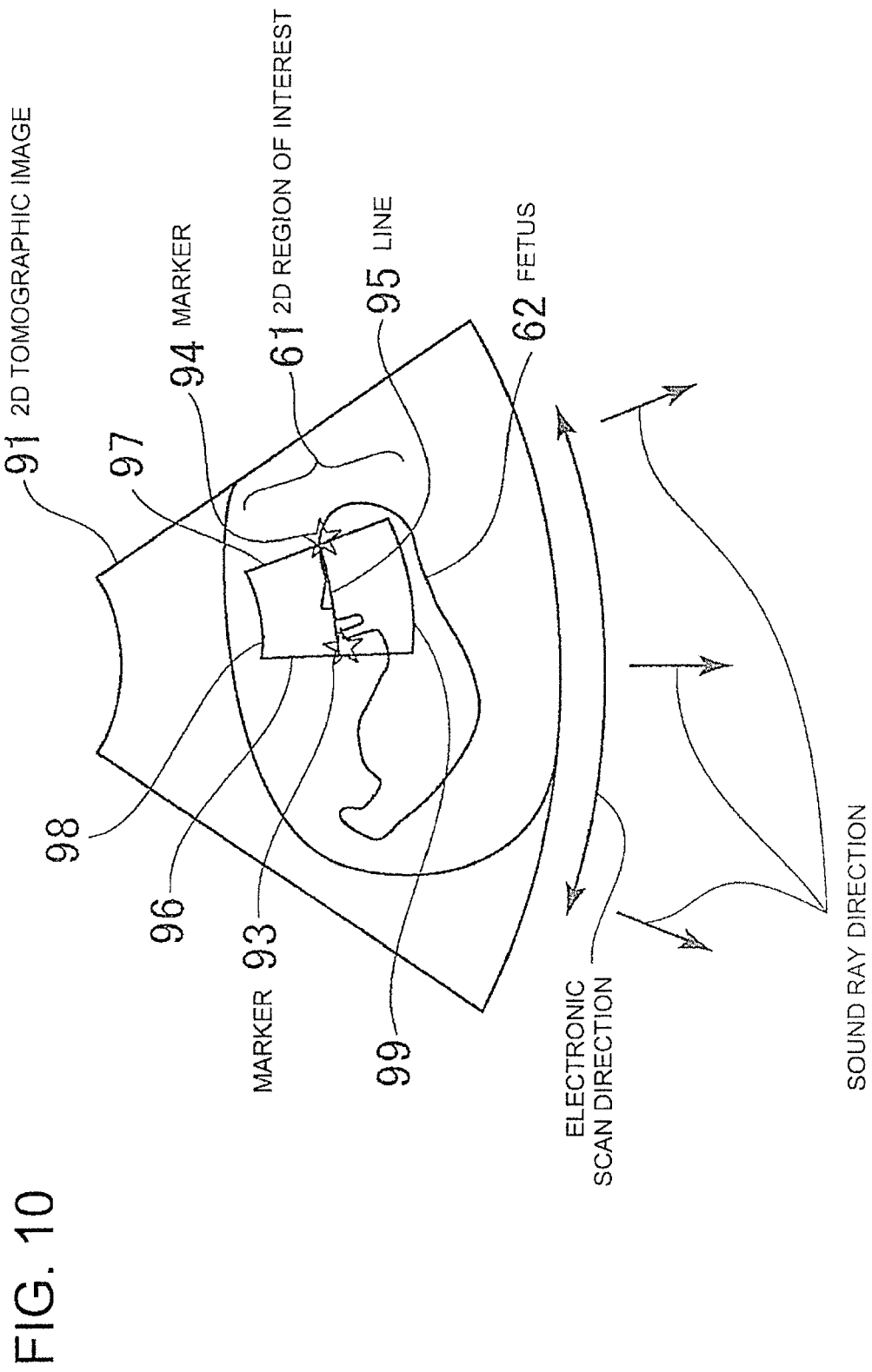
FIG. 10 is an explanatory view showing a typical example of a 2D region of interest generated from markers in a 2D tomographic image.

After that, the 2D region-of-interest generating means 43 generates a 2D region of interest 61 inside the 2D tomographic image 91 according to the markers 93 and 94 and the line 95 (Step S803). FIG. 10 is an explanatory view showing an example of the 2D region of interest 61 generated by the 2D region-of-interest generating means 43. The 2D region-of-interest generating means 43 generates the 2D region of interest 61 as a region in which the line 95 is in the vicinity of its center.

Here, the 2D region-of-interest generating means 43 generates, for example, a 2D region of interest 61 enclosed by line segments 96 and 97 passing through the markers 93 and 94 in sound ray directions in which ultrasonic echoes are received and transmitted, and line segments 98 and 99 in the scan direction which make the area of the amniotic fluid 63 and fetus 62 almost equally divided with the line 95 between them. The value of the area is entered through the input section 107 by the operator.

The positions of the line segments 98 and 99 in the scan direction can also be such that the lengths of the line segments 96 and 97 are equal with the markers 93 and 94 between them. Also, the abovementioned area and line segment length may be specified by the operator through the input section 107.

Figure 11A:
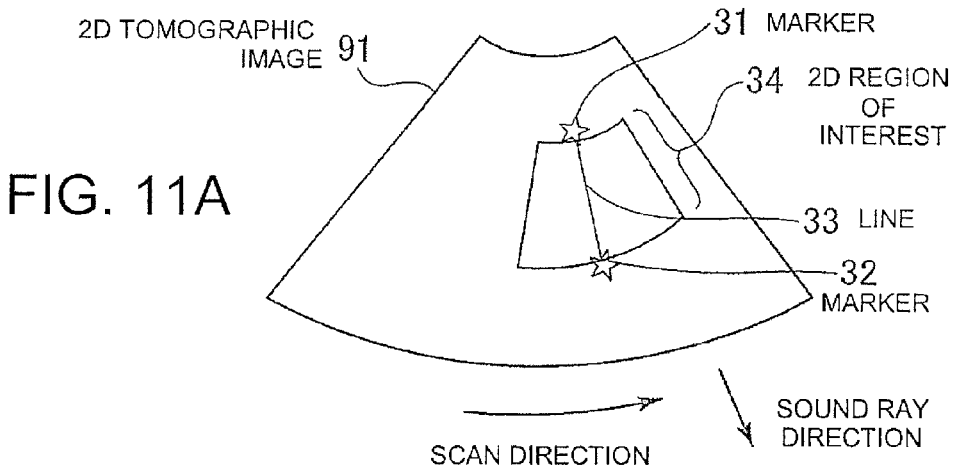
FIGS. 11A, 11B, and 11C are explanatory views showing another example of a 2D region of interest generated from markers.
Figure 11B:
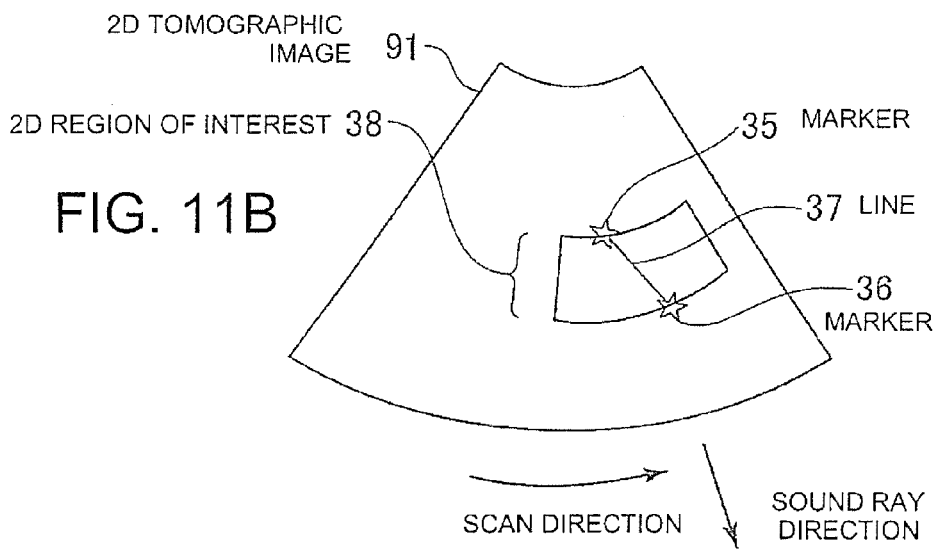
Figure 11C:
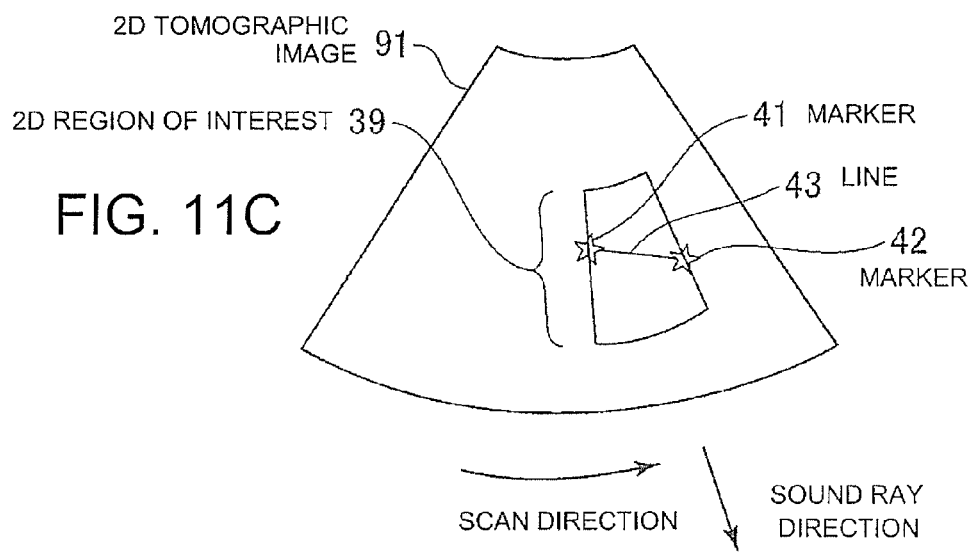

FIGS. 11A, 11B, and 11C are explanatory views showing variations of the 2D region of interest 61 generated by the 2D region-of-interest generating means 43. Although the line 95 shown in the 2D tomographic image 91 of FIG. 10 is set so as to be almost oriented in the electronic scan direction, it can be oriented in different directions in the plane of the 2D tomographic image 91 depending on the orientation of the body surface to be stereoscopically displayed. The generated 2D region of interest 61 varies depending on the orientation of the line 95 in the 2D tomographic image 91.

FIG. 11A is an explanatory view showing a 2D region of interest 34 in which markers 31 and 32 indicating the boundary of a massive tissue are arranged along the sound ray direction and line 33 connecting the markers 31 and 32 is oriented in the sound ray direction. The 2D region of interest 34 is formed by such line segments in the scan direction that the line 33 bisects the area in the electronic scan direction, and line segments which connect the ends of these line segments.

FIG. 11B is an explanatory view showing a 2D region of interest 38 in which markers 35 and 36 indicating the boundary of a massive tissue are arranged with an angle with respect to the sound ray direction and the acute-angled portion where the angle formed between line 37 connecting the markers 35 and 36 and the sound ray direction does not exceed 90 degrees is oriented in the sound ray direction. The 2D region of interest 38 is formed by such line segments passing through the markers 35 and 36 in the scan direction that the line 37 bisects the area in the electronic scan direction, and line segments in the sound ray direction which connect the ends of these line segments.

FIG. 11C is an explanatory view showing a 2D region of interest 39 in which markers 41 and 42 indicating the boundary of a massive tissue are arranged with an angle with respect to the sound ray direction and the acute-angled portion where the angle formed between line 43 connecting the markers 35 and 36 and the sound ray direction does not exceed 90 degrees is oriented in a direction opposite to the sound ray direction. The 2D region of interest 39 is formed by such line segments passing through the markers 41 and 42 in the sound ray direction that the line 43 bisects the area in the sound ray direction, and line segments in the scan direction which connect the ends of these line segments.

Referring again to FIG. 8, the 3D region-of-interest generating means 44 generates a 3D region of interest 67 using the generated 2D region of interest 61 (Step S804). The 3D region-of-interest generating means 44 expands the 2D region of interest 61 in the mechanical scan direction using information on the angle of oscillation from the center in the mechanical scan direction of the probe array 17. Consequently a 3D region of interest 67, a reduced form of the 3D region shown in FIG. 5, is formed in the image memory 104 and this process is ended.

Here, since 2D regions of interest 61, 34, 38 and 39 in which lines 95, 33, 37 and 43 constituting massive tissue boundaries are in the vicinity of the center are set in the sectional plane A 81 located at the home position, a 3D region of interest obtained by expanding a 2D region of interest in the mechanical scan direction includes the massive tissue boundary to the maximum extent possible. How the massive tissue boundary spreads in the mechanical scan direction from the home position as the center is not determined, the massive tissue boundary does not always spread all over a sectional plane corresponding to the sectional plane C 83 in the 3D region of interest.

After this process is ended, the image processor 60 stereoscopically displays the surface image 66 on the display section 106 using the surface image extracting means 73 and stereoscopic display generating means 74.

As explained so far, in this embodiment, in setting a 2D region of interest 61, markers 93 and 94 are set on a linear surface of the massive tissue, and a 2D region of interest 61 whose area or length is almost equally divided by line 95 connecting the markers 93 and 94 is generated, so that the surface image 66 is included to the maximum extent in the 3D region of interest 67 generated by expanding the 2D region of interest 61 at the home position in the mechanical scan direction and a stereoscopic display is quickly made without the need for the operator to repeat the procedure for rendering an optimum stereoscopic image.

Although this embodiment uses an ultrasonic probe 10 which mechanically scans with a one-dimensional array of piezoelectric elements, an ultrasonic probe which has a 2D probe array with piezoelectric elements two-dimensionally arranged on a plane may be used instead. In this case, 3D tomographic image data in the 3D region 8 can be captured only by an electronic scan.

Furthermore, although the image processor 60 is included in the control section 108 in this embodiment, alternatively an image processing apparatus with a computing part and an image memory may be provided separately from the ultrasonic imaging apparatus so that this image processing apparatus is used to perform the same function as the image processor 60.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic imaging apparatus comprising:
   a 3D tomographic image data capturing device configured to capture 3D tomographic image data from a 3D region inside a subject;
   a region-of-interest setting device configured to set a 3D region of interest corresponding to the 3D region in an image memory that stores the 3D tomographic image data;
   a surface image extracting device configured to extract data on a surface image of a tissue included in the 3D region using the 3D tomographic image data, wherein the surface image is within the 3D region of interest;
   a stereoscopic display generating device configured to generate stereoscopic display data to display the surface image data stereoscopically;
   a plane formation device configured to form 2D image data according to the 3D tomographic image data; and
   a display device configured to display the stereoscopic display data, wherein said region-of-interest setting device is further configured to:
   display a 2D tomographic image of a 2D region including the tissue on said display device using the 2D image data;
   receive a manual setting of two markers indicating a periphery of the tissue in the 2D tomographic image;
   define a tissue boundary as a line connecting the two markers in the 2D tomographic image;

define a first line segment on a first side of the tissue boundary line and a second line segment on a second side of the tissue boundary line such that the tissue boundary line is substantially equidistance between the first line segment and the second line segment to at least partially define a 2D region of interest; and generate the 3D region of interest by expanding the 2D region of interest in the 2D tomographic image in a mechanical scan direction and including the tissue boundary in the vicinity of the center.

2. An ultrasonic imaging apparatus comprising:

a 3D tomographic image data capturing device configured to capture 3D tomographic image data from a 3D region inside a subject;

a region-of-interest setting device configured to set a 3D region of interest corresponding to the 3D region in an image memory that stores the 3D tomographic image data;

a surface image extracting device configured to extract data on a surface image of a tissue included in the 3D region using the 3D tomographic image data, wherein the surface image is within the 3D region of interest;

a stereoscopic display generating device configured to generate stereoscopic display data to display the surface image data stereoscopically; and a display device configured to display the stereoscopic display data, wherein said region-of-interest setting device comprises:

a tissue cross section display device configured to display a 2D tomographic image of a 2D region including the tissue;

a tissue boundary setting device configured to receive a manually set linear tissue boundary on a periphery of the tissue appearing in the 2D tomographic image;

a marker setting device configured to set two markers on the 2D tomographic image, to define the tissue boundary as a line connecting the two markers, and to define a first line segment on a first side of the tissue boundary line and a second line segment on a second side of the tissue boundary line such that the tissue boundary line is substantially equidistance between the first line segment and the second line segment;

a 2D region-of-interest generating device configured to generate a 2D region of interest based on the two markers, the first line segment, and the second line segment and including the tissue boundary in the vicinity of the center; and a 3D region-of-interest generating device configured to generate a 3D region of interest by expanding a region of interest of the same shape as the 2D region of interest in a direction orthogonal to the 2D region.

3. The ultrasonic imaging apparatus of claim 2, further comprising an orthogonal 3-sectional plane formation device configured to form tomographic image data on three orthogonal sectional planes which are orthogonal to each other in the 3D region.

4. The ultrasonic imaging apparatus of claim 3, wherein said display device is configured to display tomographic image data on the three orthogonal sectional planes.

5. The ultrasonic imaging apparatus of claim 2, wherein said 3D tomographic image data capturing device comprises:

a probe array comprising a plurality of piezoelectric elements that are one-dimensionally arranged in one of an arcuate pattern and a linear pattern; and an ultrasonic probe configured to manually scan said probe array repeatedly in a mechanical scan direction orthogonal to a direction of the one-dimensional arrangement.

6. The ultrasonic imaging apparatus of claim 5, wherein said orthogonal 3-sectional plane formation device is configured to form, as one of the three orthogonal sectional planes, a sectional plane including an electronic scan direction as the direction of the one-dimensional arrangement and, as another of the three orthogonal sectional planes, a plane including the mechanical scan direction.

7. The ultrasonic imaging apparatus of claim 6, wherein said tissue cross section display device is configured to orient the 2D region such that the 2D region coincides with the sectional plane including the electronic scan direction, among the three orthogonal sectional planes.

8. The ultrasonic imaging apparatus of claim 2, wherein said 3D tomographic image data capturing device comprises an ultrasonic probe having a 2D probe array in which piezoelectric elements are two-dimensionally arranged in a planar pattern.

9. The ultrasonic imaging apparatus of claim 2, wherein said 2D region-of-interest generating device is configured to generate a 2D region of interest comprising a first region and a second region of equal areas with the tissue boundary between them, the first region at least partially defined by the first line segment and the tissue boundary line and the second region at least partially defined by the second line segment and the tissue boundary line.

10. The ultrasonic imaging apparatus of claim 2, wherein said 2D region-of-interest generating device is configured to generate a 2D region of interest comprising two regions of approximately equal lengths in a direction orthogonal to the tissue boundary in the 2D tomographic image with the tissue boundary between them.

11. The ultrasonic imaging apparatus of claim 2, wherein said 3D region-of-interest generating device is configured to position the 2D region of interest centrally in a direction orthogonal to the 2D region of interest in the 3D region of interest.

12. The ultrasonic imaging apparatus of claim 2, wherein said 3D region-of-interest generating device comprises an input device configured to receive an entered size to which the 2D region of interest is expanded in a direction orthogonal to the 2D region of interest.

13. The ultrasonic imaging apparatus of claim 2, wherein said surface image extracting device comprises an input device configured to receive an entered threshold used in extracting surface image data from the 3D tomographic image data in the 3D region of interest, using pixel values.

14. The ultrasonic imaging apparatus of claim 2, wherein said stereoscopic display generating device is configured to display the surface image data in shaded form.

15. The ultrasonic imaging apparatus of claim 2 further comprising a plane formation device configured to form three 2D tomographic images from the 3D tomographic image data, wherein the three 2D tomographic images includes a first 2D tomographic image in a first plane, a second 2D tomographic image in a second plane orthogonal to the first plane, and a third 2D tomographic image in a third plane orthogonal to the first and second planes.

16. The ultrasonic imaging apparatus of claim 15, wherein said surface image extracting device is configured to obtain a contour from each of the three 2D tomographic images.

17. The ultrasonic imaging apparatus of claim 16, wherein said surface image extract device is configured to combine the contours to generate the surface image.

18. The ultrasonic imaging apparatus of claim 2, wherein the 2D region of interest is partially enclosed by a third line segment through a first marker of the two markers and a fourth line segment through a second marker of the two markers.

19. The ultrasonic imaging apparatus of claim 18, wherein the 2D region of interest is further enclosed by the first line segment and second line segment each intersecting the third and fourth line segment, wherein the tissue boundary line connecting the two markers intersects the third line segment and the fourth line segment.

20. An image processing apparatus comprising:
- an image memory configured to store 3D tomographic image data of a subject;
- a region-of-interest setting device configured to set a 3D region of interest in a 3D region in which the 3D tomographic image data is captured;
- a surface image extracting device configured to extract data on a surface image of a tissue included in the 3D region of interest using the 3D tomographic image data;
- a stereoscopic display generating device configured to generate stereoscopic display data to display the surface image data stereoscopically; and
- a display device configured to display the stereoscopic display data, wherein said region-of-interest setting device comprises:
  - a tissue cross section display device configured to display a 2D tomographic image of a 2D region including the tissue;
  - a tissue boundary setting device configured to receive a manually set linear tissue boundary on a periphery of the tissue appearing in the 2D tomographic image;
  - a marker setting device configured to set two markers on the 2D tomographic image, to define the tissue boundary as a line connecting the two markers, and to define a first line segment on a first side of the tissue boundary line and a second line segment on a second side of the tissue boundary line such that the tissue boundary line is substantially equidistance between the first line segment and the second line segment;
  - a 2D region-of-interest generating device configured to generate a 2D region of interest based on the two markers, the first line segment, and the second line segment and including the tissue boundary in the vicinity of the center; and
  - a 3D region-of-interest generating device configured to generate a 3D region of interest by expanding a region of interest of the same shape as the 2D region of interest in a direction orthogonal to the 2D region.

* * * * *